United States Patent [19]
Emerson et al.

[11] Patent Number: 5,849,179
[45] Date of Patent: Dec. 15, 1998

[54] AUTOMATIC APPARATUS FOR OBTAINING EQUILIBRATION SAMPLES OF DIALYSATE

[75] Inventors: Paul Emerson, St. Louis Park; Prakash Keshaviah, Minnetonka; David A. Luhring, Savage, all of Minn.

[73] Assignee: Baxter International Inc., Deerfield, Ill.

[21] Appl. No.: 650,414

[22] Filed: May 20, 1996

Related U.S. Application Data

[63] Continuation-in-part of Ser. No. 239,936, May 9, 1994, Pat. No. 5,518,623, which is a continuation of Ser. No. 959,922, Oct. 13, 1992, abandoned.

[51] Int. Cl.$^6$ .......................... B01D 61/30; B01D 61/32
[52] U.S. Cl. .................. 210/87; 210/96.2; 210/195.2; 210/433.1; 210/646; 210/929; 604/5
[58] Field of Search .................. 210/87, 96.2, 195.2, 210/369, 433.1, 434, 636, 644, 646, 929, 93, 424, 321.6; 604/4–63; 205/780.5; 204/403, 406, 409, 415; 436/108; 422/68.1

[56] References Cited

U.S. PATENT DOCUMENTS

| | | | |
|---|---|---|---|
| 3,802,562 | 4/1974 | Kozlov et al. | 210/96.2 |
| 3,919,075 | 11/1975 | Parc et al. | 210/644 |
| 3,990,973 | 11/1976 | Boag et al. | 210/96.2 |
| 4,112,768 | 9/1978 | Holland et al. | |
| 4,244,787 | 1/1981 | Klein et al. | |
| 4,370,983 | 2/1983 | Lichtenstein | 210/929 |
| 4,508,622 | 4/1985 | Polaschegg et al. | 210/96.2 |
| 4,668,400 | 5/1987 | Veech | 210/647 |
| 4,686,479 | 8/1987 | Young et al. | |
| 4,722,798 | 2/1988 | Goss | 210/646 |

(List continued on next page.)

FOREIGN PATENT DOCUMENTS

| | | |
|---|---|---|
| 80109767 | 8/1992 | China . |
| 0 437 789 A2 | 7/1991 | European Pat. Off. . |
| 0 504 772 A2 | 3/1992 | European Pat. Off. . |
| 0 495 412 A1 | 7/1992 | European Pat. Off. . |
| 0532433 | 9/1992 | European Pat. Off. . |
| 0621046 | 2/1994 | European Pat. Off. . |
| 2712822 | 11/1993 | France . |
| 3436748 A1 | 7/1985 | Germany . |

OTHER PUBLICATIONS

*Quantitation of Dialysis*, "Refining the Model of Urea Kinetics: Compartment Effects," Thomas A. Depner, pp. 147–153, undated.

Blackwell Scientific Publications, Inc., *Artificial Organs*, "Kt/V and protein Catabolic Rate Determination from Serial Urea Measurement in the Dialysate Effluent Stream," Laurie J. Garred, Bonny DiGiuseppe, Winston Chand, William McCready, and Bernard Canaud, pp. 248–255, undated.

(List continued on next page.)

*Primary Examiner*—Joseph W. Drodge
*Attorney, Agent, or Firm*—Thomas S. Borecki; Charles R. Mattenson; A. Jose Cortina

[57] ABSTRACT

An improved on-line, real time hemodialysis monitoring system for hemodialysis treatment, quantitates the rate and amount of a constituent, such as urea, removed during the hemodialysis treating by measuring the constituent concentrations as a function of time in the spent dialysate effluent from a hemodialysis machine. A quantity of the spent dialysate effluent is removed from the dialysate effluent waste line periodically for testing. A urea concentration time profile can be analyzed to determine the urea removal, KT/V, URR, SRI, and normalized protein catabolic rate (nPCR) indices. The hemodialysis monitoring system preferably can obtain a dialysate sample equilibrated with the blood prior to the start of a hemodialysis treatment. In a further aspect of the hemodialysis monitoring system includes a device for conducting two-pool analysis for taking into account the constituent concentration differences in the extracellular and intracellular spaces in the hemodialysis patient during the hemodialysis treatment to determine the intercompartmental transfer coefficient $K_I$ of a patient, which allows more precise adjustment of the hemodialysis prescription for the patient.

11 Claims, 10 Drawing Sheets

U.S. PATENT DOCUMENTS

| | | | |
|---|---|---|---|
| 4,955,857 | 9/1990 | Shettigar | 604/5 |
| 5,024,756 | 6/1991 | Sternby | 210/96.2 |
| 5,100,554 | 3/1992 | Polaschegg | 210/647 |
| 5,110,477 | 5/1992 | Howard et al. | 210/647 |
| 5,142,271 | 8/1992 | Bailey et al. . | |
| 5,230,702 | 7/1993 | Lindsay et al. . | |
| 5,247,434 | 9/1993 | Peterson et al. | 210/646 |
| 5,518,623 | 5/1996 | Keshaviah et al. | 210/646 |
| 5,670,057 | 9/1997 | Chen et al. | 210/646 |
| 5,685,988 | 11/1997 | Malchesky | 210/646 |
| 5,698,083 | 12/1997 | Glass | 436/108 |
| 5,725,773 | 3/1998 | Pulaschegg | 210/646 |

OTHER PUBLICATIONS

*Abstracts of the XII Annual CAPD Conference*, vol. 12, Supplement 1, 1992, "Peritoneal Dialysis International."

E. Klein and J.G. Montalvo, Jr., *International Journal of Artificial Organs*, vol. 1, No. 3, pp. 116–122 and No. 4, pp. 175–180, 1978, "Continuous Monitoring of Urea Levels During Hemodialysis."

*Official Journal of the International Society for Artificial Organs*, "Artificial Organs", Aug. 1991, vol. 15, No. 4, p. 285.

| Patient # | Lab BUN | Plasma water corrected BUN | BioStat Auto Equilibration |
|---|---|---|---|
| 300JF | 77.5 | 83.3 | 77.1 |
| 301MH | 77.5 | 83.3 | 79.8 |
| 301CC | 51.0 | 54.8 | 54.0 |
| 303LM | 63.5 | 68.3 | 64.6 |
| 304IK | 79.0 | 84.9 | 77.2 |
| 305FU | 28.0 | 30.1 | 28.7 |
| 306HJ | 69.0 | 74.2 | 69.5 |
| 307LL | 22.0 | 23.7 | 22.6 |
| 308DB | 47.0 | 50.5 | 44.9 |
| 309JM | 82.5 | 88.7 | 78.2 |
| 310RH | 61.0 | 65.6 | 60.5 |
| 311JH | 58.5 | 62.9 | 62.4 |
| 312LJ | 38.0 | 40.9 | 40.9 |
| 313KS | 44.5 | 47.8 | 45.1 |
| 314MC | 63.5 | 68.3 | 66.3 |
| 315BG | 44.0 | 47.3 | 43.3 |
| 316LS | 65.0 | 69.9 | 65.4 |
| 317JW | 40.0 | 43.0 | 42.0 |
| 318DS | 50.0 | 53.8 | 50.8 |
| 319EW | 79.5 | 85.5 | 83.0 |

FIG. 12

AUTOMATIC APPARATUS FOR OBTAINING EQUILIBRATION SAMPLES OF DIALYSATE

CROSS REFERENCE TO RELATED APPLICATIONS

This application is a continuation-in-part of application Serial No. 08/239,936, filed May 9, 1994, now U.S. Pat. No. 5,518,623 which is a continuation of application Ser. No. 07/959,922, filed Oct. 13, 1992, and now abandoned.

FIELD OF THE INVENTION

The present invention relates generally to hemodialysis machines and methods for on-line, real time monitoring of the effectiveness of the hemodialysis treatment, and more particularly, for obtaining the intercompartmental transfer coefficient for two pool kinetics in hemodialysis.

BACKGROUND OF THE INVENTION

The use of dialyzers with hemodialysis machines to remove blood-borne toxins and by-products of metabolism has been conventional for many years. Typically, such a dialyzer contains a pair of chambers separated by a semi-permeable membrane. Blood is perfused through the first chamber returned to the patient. The dialysate solution is simultaneously circulated in the opposite direction through the second chamber. A concentration gradient thereby is established which causes waste products carried in the blood to diffuse through the semipermeable membrane and into the dialysate solution to form the dialysate effluent.

The principle of hemodialysis has been refined extensively. A number of semipermeable, hollow fiber membranes are now utilized in dialyzers to greatly increase the total membrane surface area to facilitate diffusion across the membrane structure. The hollow fiber membranes include a variety of materials including, for example, cellulose acetate, cellulose triacetate, polyacrylonitrile, polysulfone, and regenerated cellulose.

One of the most basic considerations in treating a patient with hemodialysis revolves around treatment adequacy, for instance, the length of time a given patient should be dialyzed on a given day. A number of medically adverse effects may result from an inadvertent failure to sufficiently dialyze the patient. At the present time, the average dialysis patient has a life expectancy of only about five years. One reason these patients tend to have a short life expectancy is the deleterious effect of a chronic buildup of various toxins that either are not eliminated at all, i.e., do not pass through the hollow fibers, or are not sufficiently reduced to nontoxic levels. The identity of many of these supposed toxins is not known, although those species known to be eliminated in urine, such as urea, creatinine, phosphate, hydrogen ions, etc., are associated with serious medical consequences when permitted to accumulate in excess of normal levels.

A number of factors can have a substantial effect on treatment adequacy. For example, it is common practice in the field of hemodialysis to reuse the dialyzers. There is technology available for cleaning, disinfecting, or sterilizing used dialyzers, for example, as illustrated in U.S. Pat. No. 4,695,385. Eventually, however, an individual dialyzer must be discarded because it loses its dialyzing competency. At the present time, the competency of dialyzers is difficult to assess and, therefore, often is not rigorously monitored, and a dialyzer cartridge is often not discarded until it visually appears unclean after reprocessing, or when fiber bundle volumes or ultrafiltration rates are reduced below a predetermined threshold. It now is known that severe dialyzer dysfunction can occur even when appearance, fiber bundle volume, and ultra filtration rates are normal, as reported by Delmez et al., "Severe dialyzer dysfunction during reuse," *Kidney International*, 35:244 (1989). It is also known that dialyzer competency can not be accurately predicted by the age of the dialyzer cartridge or the number of uses.

Notwithstanding the condition of the dialyzer, one measure of adequacy of dialysis for the individual patient during a given treatment is calculated from the following equation:

$$KT/V \geq 1.0$$

V is the volume of distribution of urea which is approximately equal to total body water volume. V is sometimes derived for an individual patient from height, weight, and sex. K is the effective urea clearance of the particular dialyzer in use in milliliters (ml) of blood cleared of urea each minute. T is the treatment time. K is often obtained from the typical product insert enclosed with a case of dialyzers, and contains a graph of urea clearance versus blood flow rate obtained by random testing of a sample of dialyzers from a particular manufacturing lot. Upon incorporating these values into the above equation, the minimum treatment time can be calculated for a given KT/V value. Other parameters that may be varied to achieve adequate dialysis include blood flow rate, dialysis solution flow rate, and dialyzer performance.

It has been determined empirically that KT/V values of about 0.8 or greater are associated with low levels of morbidity. See Gotch, L. A., Sargent, J. A. *Kidney International*, 28:526–537 (1985). Even with the use of new dialyzers there is some risk that a unit selected from a particular lot will have a significantly lower K value than the value indicated in the product insert. The patient receiving treatment from such a dialyzer is therefore at risk of being under-dialyzed. The likelihood of under-dialysis increases upon reuse of the dialyzer because of the definite but unquantified loss of dialyzer competence with each successive use. Under-dialysis also may occur because of incompetency of access to the patient's circulation. Because of incompetency of the patient's blood access, desired blood flow rates may not be achieved which also can result in under-dialysis.

Other parameters than KT/V have also been determined to assess the adequacy of dialysis. Among these are the Urea Reduction Ratio (URR) and Solute Removal Index (SRI). URR is defined as $1-(C_B)pre/(C_B)_{post}$. An ideal dialysis treatment will have a URR greater than 0.75, while a poor dialysis treatment will have a URR less than 0.50. Unfortunately, URR does not take into account generation of urea during dialysis, ultrafiltration, or the two-pool nature of removal. Consequently, SRI has been proposed as a generalized version of URR, which does account for these effects. SRI is defined as the amount of urea removed during a treatment as a fraction of the total body store. Like URR, a good dialysis treatment will have an SRI value greater than 0.75, while a poor dialysis treatment will have an SRI less than 0.50. Potentially, SRI, (unlike KT/V), can indicate the adequacy of a dialysis treatment, irrespective of modality (i.e., peritoneal or hemodialysis), and intermittence. Neither URR or SRI, however, have been validated as extensively as KT/V as measures of dialysis adequacy.

Although the KT/V, URR, and SRI indices are indicative of urea removal and appear to correlate to therapy failure, that is not tantamount to saying that urea is a toxic metabolite. There is early literature to suggest that urea is not toxic, per se. However, urea is a major metabolite of protein catabolism and serves as a convenient marker to monitor treatment adequacy.

Urea has a molecular weight of 60 Daltons, while some of the other protein catabolites may be much larger. It has, therefore, become a subject of controversy whether the relationship between KT/V and morbidity, established with the tighter cellulosic membranes, is applicable to the more open membranes used for hemofiltration and high flux hemodialysis or to the natural peritoneal membrane.

There is a considerable body of literature on the urea kinetic model. Computer programs, programmable calculators, and time-shared computer services, have been developed to make urea kinetics more accessible to the dialysis clinician. It has recently been shown (Lindsay et al., 1989) that KT/V values of less than 0.8 may be associated with a low dietary protein intake that is intractable to nutritional counseling. However, increasing the KT/V to 1.0 or higher, in conjunction with nutritional counseling, is effective in improving dietary protein intake. As low dietary protein intake may be associated with increased morbidity, monitoring of the KT/V, and nPCR are useful adjuncts to other clinical assessments of the dialysis patient.

Traditional urea kinetics entails numerous measurements and is considered mathematically complex by dialysis clinicians. The various measurements required for accurate kinetic measurements are summarized in Table 1.

TABLE 1

MEASUREMENTS REQUIRED FOR UREA KINETIC CALCULATIONS

Pre dialysis BUN ($C_1$)
Post dialysis BUN ($C_2$)
Pre-dialysis BUN for next dialysis ($C_3$)
Dialyzer clearance (K)
Blood flow rate
Arterial BUN
Venous BUN
dialysate flow rate (effluent) ($Q_{do}$)
Access recirculation
Peripheral BUN
Residual renal function
Urine volume
Urine concentration
Dialysis duration ($t_d$)
Off dialysis duration ($t_{od}$)
Ultrafiltration rate
Weight gain between dialyses Each of these measurements is associated with finite error and the cumulative effect of these errors may lead to unrealistic urea kinetic parameters.

Prior art hemodialysis machines have not had the capability of on-line monitoring of the hemodialysis treatment. Further, the prior art techniques generally have required the taking of blood samples from the hemodialysis patient.

In considering the invention it is noted that, for example, the Baxter BioStat 1000™ urea monitor, on which the invention may be employed, is a noninvasive device which connects to the dialysate outflow of the dialyzer and measures the concentration of urea in discrete samples of dialysate. From these concentrations, the amount of urea removed from a patient and various kinetic parameters, such as KT/V (clearance time divided by volume of distribution), can be, and are, calculated. In order to separate clearance (K) from volume (V), an equilibration sample is taken prior to the start of dialysis. This involves placing the dialysis machine into dialysis bypass and starting blood flow and ultrafiltration for up to 10 minutes while the concentration of urea in the blood equilibrates with the concentration of urea in the dialysate. Because the process is under operator control, the amount of time and/or ultrafiltration can be either too little or too much. While this procedure is possible for most dialysis machines, there are some machines that do not allow an equilibration sample to be obtained.

The device according to the invention provides an automated bypass and equilibration function which automates the current manual process of obtaining a predialysis equilibration sample. The device also allows the equilibration sample to be obtained with machines that are incompatible with the manual procedure.

In accordance with the invention, a desirable and reliable non-invasive, on-line real time monitoring of the hemodialysis treatment would be provided, both before and while the patient is attached to the hemodialysis machine. The treatment, when based upon urea kinetics, preferably would require measurements of effluent dialysate concentrations and flow but not of blood samples. The treatment would yield as outputs the KT/V, URR, and SRI indices of therapy adequacy, the urea removal and the normalized protein catabolic rate (nPCR), which then could be utilized to assess dietary compliance and adequacy of treatment in real time. Equilibration is achieved automatically and reliably prior to commencing dialysis to result in a highly reliable treatment regimen.

SUMMARY OF THE INVENTION

The invention of U.S. application Ser. No. 08/239,936, filed May 9, 1994, of which this application is a continuation-in-part, is directed to an improved on-line, real time hemodialysis monitoring method and system for hemodialysis machines. The hemodialysis monitoring system quantitates the rate and amount of urea removed during the hemodialysis treatment by measuring the urea concentration in the spent dialysate effluent as a function of time. The dialysate effluent line from the hemodialysis machine is sampled periodically to remove a small volume of the spent dialysate effluent when a sufficient fluid flow is sensed. The urea concentration-time profile is determined and analyzed to determine the urea removal, KT/V, URR, and normalized protein catabolic rate (nPCR). The hemodialysis monitoring system and urea monitor configuration can be changed to allow equilibration of blood with the dialysate effluent prior to the start of and at the end of a hemodialysis treatment. The hemodialysis monitoring system also can include a two-pool analysis, taking into account the different degree of urea depletion from the extracellular and intracellular spaces in the hemodialysis patient during treatment. This allows the calculation of the solute removal index (SRI).

The present invention adds to the invention of application Ser. No. 08/239,936, by providing a method and device for obtaining the intercompartmental transfer coefficient ($K_I$) for a patient undergoing hemodialysis treatment.

In accordance with the invention there is provided a method through which the dialysate flow bypasses the dialyzer with the blood pump running so that diffusion continues to occur, and an ultrafiltrate from the blood passes into the dialysate compartment of the dialyzer. Eventually, due to this diffusion and convection, the dialysate in the dialyzer reaches a metabolite concentration equal to the patient's plasma water concentration. At this time the dialysate may be sampled and measured. This process may occur prior to, during, and/or after the hemodialysis treatment. When such a concentration is obtained before dialysis, "K" and "V" may be separated. When at least one concentration is obtained after dialysis the intercompartmental transfer coefficient $K_I$ may be reliably determined.

In another aspect, the invention involves a method of obtaining an equilibrated dialysate sample whose metabolite concentration is the same as that of the plasma water of the blood of a patient. A dialysate flow to a dialyzer is stopped while the blood pump is allowed to run and ultrafiltration to take place from the blood of a patient. The concentration of a selected metabolite, typically urea, is measured initially, after partial equilibration, to obtain a first sample from which the concentration is measured. The metabolite concentration is measured in an obtained second sample after a specified time has passed. The two measured concentrations are compared, and sampling/measuring is continued until the difference between two successive samples is less than a specified amount.

In yet another aspect, the invention relates to a method for automatically obtaining the intercompartmental transfer coefficient for a patient undergoing hemodialysis with a dialysis machine. The method of obtaining an equilibrated dialysate sample, as discussed above, is first conducted. Thereafter, the blood pump continues to run with the dialysis machine in bypass mode, and samples which have been equilibrated are taken at regular time intervals. The rate of change of metabolite concentration, typically urea, after the end of a hemodialysis treatment is determined from the measurements. The ratio of the extra- and intra-cellular volume ($R_V$) of a patient is determined from the rate of change of metabolite concentration in the patient's blood.

Preferably blood concentration ($C_{bew}$) of metabolite is measured at intervals during dialysis. By using non-linear fitting techniques, $K_I$ and/or the intra- and extra-cellular volumes of a patient can be obtained from the obtained equilibration samples and the blood concentration ($C_{bew}$) measurements. Yet more preferably, a pre-run equilibration sample can be obtained to separate K and V once the ratio of K/V is known. A mid-run equilibration can be obtained to estimate K. While the invention has been described in the context of periodic sampling, it can also be employed in hemodialysis machines which conduct continuous sampling. Samples at discrete time periods can be used to practice the methods of the invention.

In yet still another aspect, the invention relates to a device for conducting the above-described method. The device includes a bypass device connectable between the inlet and outlet of the dialyzer and dialysate ports of a dialysis machine. A valve is provided for selectively shunting dialysate fluid from the dialysis machine away from the dialyzer. With the blood pump still running, a positive transmembrane pressure then causes an ultrafiltrate to pass from the blood into the dialysate. Eventually, ongoing diffusion and the presence of high concentration ultrafiltrate causes the metabolite concentration of the dialysate to reach the plasma water metabolite concentration. A flow meter is provided to obtain the dialysate flow rate while it is shunted away from the dialyzer. As a consequence, the user no longer has to enter the dialysate flow rate by hand.

BRIEF DESCRIPTION OF THE DRAWINGS

These and other features and advantages of the invention will be more readily apparent upon reading the following description of a preferred exemplified embodiment of the invention and upon reference to the accompanying drawings, wherein:

FIG. 12 is a table showing clinical data using the device of the invention; and

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

Figure 1:
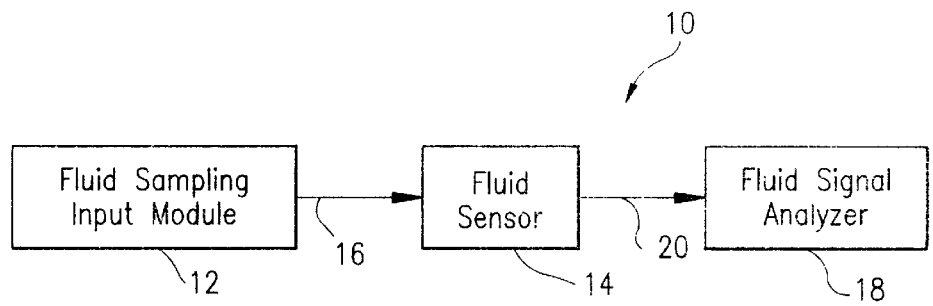
FIG. 1 is a block diagram of one embodiment of the hemodialysis monitoring system of the present invention.

Referring to FIG. 1, one embodiment of a hemodialysis monitoring system of the present invention is designated generally by the reference numeral 10. Such a system is part of a dialysis machine which is currently commercially available through Baxter Healthcare Corporation, under the trade name BioStat™ 1000. The monitor 10 includes an input module 12, which can in the preferred embodiment be a urea sensor or an appropriate sensor for sensing a different molecule or constituent to be cleared. The module 12 samples a volume of the dialysate effluent intermittently, as desired. The module 12 couples the dialysate sample volume to a sensor 14 via a line 16. The sensor 14 generates a signal which is proportional to the monitored constituent concentration and couples that signal to a constituent signal analyzer 18 via a line 20.

The module 12 can be any type of sampling device which is coupled, preferably permanently, to the dialysate effluent line (not illustrated). A preferred input module 12 is disclosed and described in copending application, docket number Ser. No. 07/960,088, filed Oct. 13, 1992, entitled "FLUID SAMPLING MODULE," filed concurrently herewith, now abandoned, which is incorporated herein by reference. The urea sensor 14 can be a sensor, such as described in U.S. Pat. No. 4,686,479, entitled "APPARATUS AND CONTROL KIT FOR ANALYZING BLOOD SAMPLE VALUES INCLUDING HEMATOCRIT," which also is incorporated herein by reference. The liquid sample is contacted with a urea sensor that includes a urease layer associated with an electrode adapted to generate output in response to ammonium ions. The urease layer converts a portion of the urea in the sample to ammonium ions, and the ions contact the electrode to generate output related to the urea concentration in the sample.

The sensor 14 is described herein, for example purposes, as a urea sensor. There are other approaches to urea sensing and any urea sensor that can measure urea concentration in the effluent dialysate line can be utilized for this purpose. The invention, therefore, is not specific to a particular type of urea sensor. Urea, however, is just one of a number of identifiable constituents generally related to uremia in a patient's blood, which can be utilized as a marker or measure of the effectiveness of the hemodialysis treatment, i.e., the removal of toxins. Such other constituents are, for example, creatinine, uric acid, phosphate, calcium, sodium, potassium, glucose, beta 2 micro globulin, among others. Other types of sensors also can be utilized in the hemodialysis monitoring system of the present invention, which sense the required fluid constituent(s) direct or indirectly.

There are also other approaches to the flow configuration of the urea sensor. The most direct configuration is location of the urea sensor in the effluent dialysate stream. Another direct configuration is taking the sample volume from the fluid stream and flowing the sample volume past the sensor. Other configurations could include:

1. Locating the sensor in the fresh inflow dialysate stream with effluent dialysate being pumped in, upstream of the sensor, in a flow injection mode.
2. Pumping inflow and outflow streams in the desired proportions for dilution past the urea sensor.
3. A flow injection scheme where a carrier buffer stream is pumped past the urea sensor with injection of effluent dialysate into this buffer stream.

Figure 2:
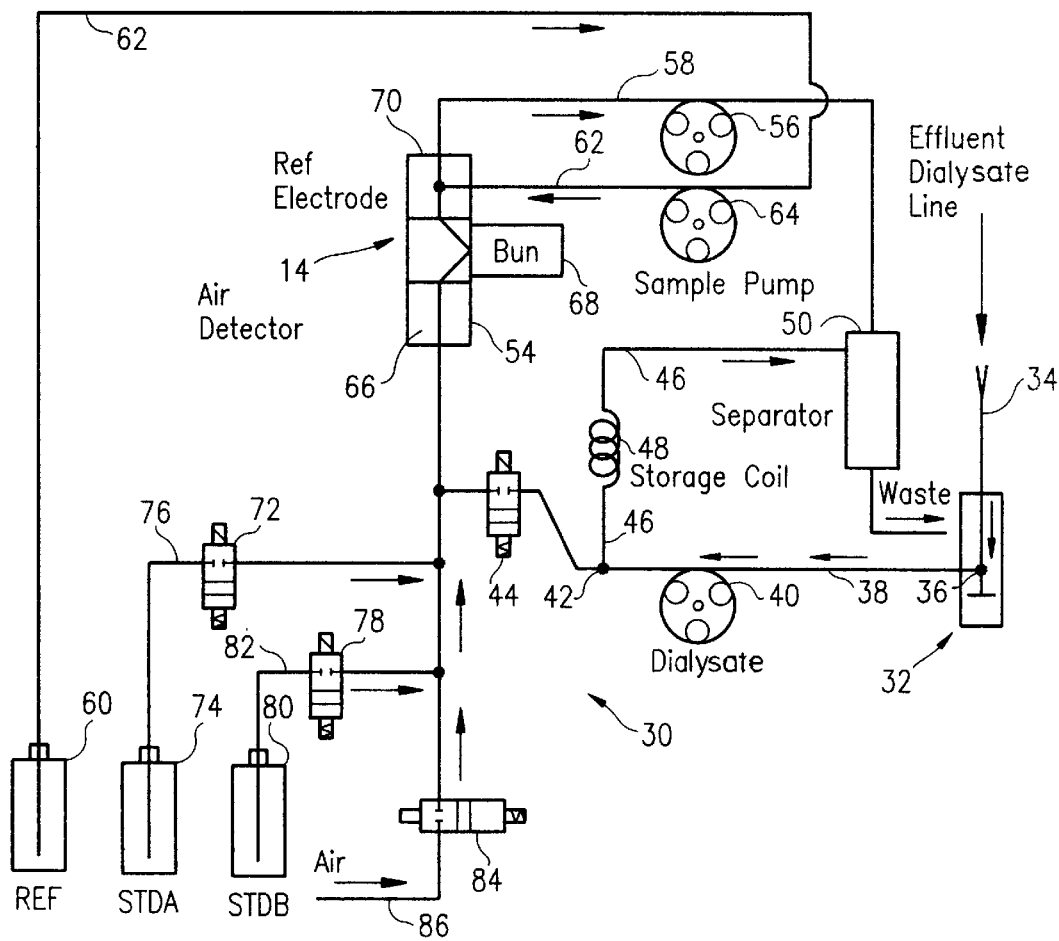
FIG. 2 is a schematic diagram of one embodiment of a portion of the hemodialysis monitoring system of FIG. 1.

One urea input/sensor module embodiment of the urea input module 12 and the urea sensor 14 of the hemodialysis monitoring system 10 of the present invention, is designated generally by the reference numeral 30 in FIG. 2. The module 30 includes a sample port 32, which preferably forms a part of a discharge or dialysate effluent line 34. The module 30 taps into the dialysate effluent line 34 via a junction 36 coupled to a sampling line 38.

The module 30 samples the dialysate effluent by activating a self-occluding peristaltic or roller pump 40. The line 38 is coupled to a junction 42 and to a normally closed valve 44. The junction 42 also is coupled to a line 46, which includes a storage coil 48. The storage coil 48 is first filled with the dialysate effluent, with the excess dialysate effluent continuing through the line 46 to a separator 50. The separator 50 includes an air gap, which prevents a backup of dialysate effluent and also prevents an electrical short through the line 52.

Once the storage coil 48 is filled, the pump 40 is stopped, which closes the line 38 from the junction 36. The valve 44 then is opened, allowing the sample dialysate to flow through the valve into a line 54, and then to and past the urea sensor 14. The sample dialysate is caused to flow by a sample pump 56, which is coupled between the urea sensor 14 and the discharge separator 50 by a line 58.

For each measurement, sample dialysate preferably is input to the urea sensor 14 and flushed through the separator 50 several times to ensure a good sample value. At the same time, the sample dialysate is pumped through the urea sensor 14, a reference fluid from a source 60 also is pumped into the urea sensor 14 via a line 62 and a second pump 64. The second pump 64 preferably can be a second roller head on the sample pump 56, but could also be a second pump coupled to operate at the same time as the sample pump 56.

As shown in more detail in U.S. Pat. No. 4,686,479, the urea sensor 14 includes an air detector 66 to determine if the sample dialysate is present in the urea sensor 14. The sensor 14 employs an electrode 68 with a membrane (not illustrated) which is specific to ammonium. The electrode 68 senses dialysate urea nitrogen (DUN) which is compared to a reference electrode 70. The signal generated by the sensor 14 then is coupled to the signal analyzer 18, as will be described in more detail hereinafter.

At the beginning of the hemodialysis treatment with a patient and periodically as desired, both a low reference standard and a high reference standard are run on the module 30 to calibrate the module 30. To calibrate the module 30 with the low standard, the valve 44 remains closed and a valve 72 is opened to allow the second pump 64 to draw in the low standard fluid from a source 74 via a line 76. The urea sensor 14 measure the low standard, which is compared to an expected range of values to ensure that the urea sensor 14 is calibrated correctly. The low standard also can be utilized to test the integrity of the system during treatment.

A similar operation is performed with a high reference standard. To run a high standard test, all the valves are closed, except for a high standard valve 78. The open valve 78 allows the second pump 64 to draw a high standard fluid from a source 80 via a line 82. The high standard fluid is measured in the urea sensor 14 and compared to an expected range of values to ensure that the urea sensor also is operating correctly at a high standard range. At the end of the low-standard cycle testing, the module 30 closes the valves 44, 72, and 78, and opens an air valve 84 for a period of time, which allows the sample pump 64 to draw air into a line 86 through the valve 84, the urea sensor 14, and out the discharge line 52. This air segment between each fluid segment helps ensure that the urea sensor 14 and the lines 54 and 58 are clean and empty of any substantial amount of residual fluid.

Figure 3:
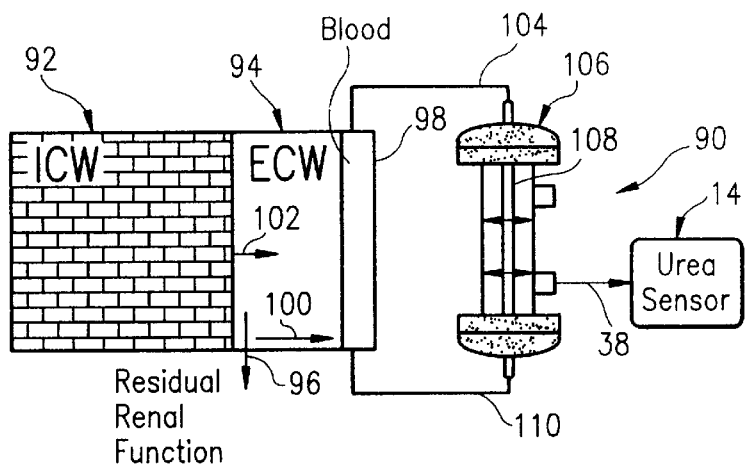
FIG. 3 is a partial block and partial schematic diagram of the fluid functions of the hemodialysis monitoring system.

Referring now to FIG. 3, a schematic embodiment of the operation of the hemodialysis monitoring system 10 of the present invention is designated generally by the reference character 90. The system 90 is depicted diagrammatically as including an intracellular space (ICW) 92 and an extracellular space (ECW) 94, which spaces are representative of the body pools in a hemodialysis patient. The hemodialysis kinetic parameters in the system 90 are calculated from the spent dialysate of a patient undergoing a typical dialysis treatment. The urea is generated in the liver, which is illustrated as being a portion of the ECW 94.

Some of the urea may be removed by the patient's kidneys, if there is a residual renal function, as indicated by an arrow 96. the majority of the urea, however, is removed by the hemodialysis treatment after first contacting the blood 98 in the ECW 94, as indicated by an arrow 100. Urea also enters the ECW 94 from the ICW 92, as indicated by an arrow 102.

The blood is removed during the hemodialysis treatment by flowing through a line 104 into a dialyzer 106. The dialyzer 106 diagrammatically includes a dialyzer membrane 108 across which urea diffuses into the dialysate. A sample volume of the dialysis effluent is removed through the line 38 and then is sensed by the urea sensor 14, as above described. The blood return to the patient via a line 110.

In a steady state condition, the total amount of urea removed during the hemodialysis treatment and sensed by the urea sensor 14 is equal to the rate of generation of urea in the patient's body in ECW 94. This allows the calculation of the normalized protein catabolic rate (nPCR) or the number of grams of urea generated per kilogram of body mass in a twenty-four hour period. Further, by knowing the concentration time profile of urea, inferences can be made about the clearance of the dialyzer 106 and the clearance-time/body water index (KT/V), which is a measure of dialysis adequacy, then can be calculated.

Figure 4:
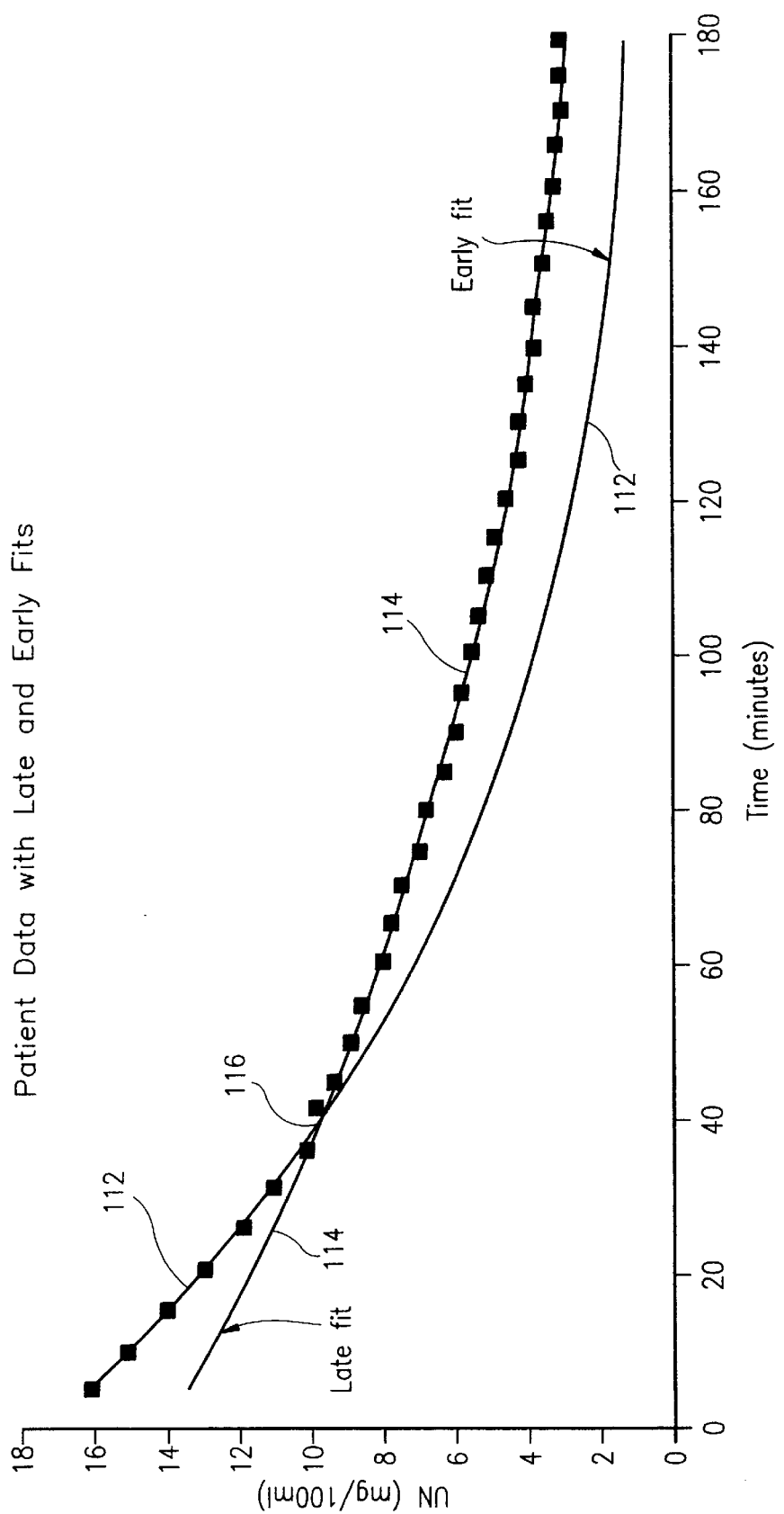
FIG. 4 is a urea concentration time profile of a typical patient illustrating a two-pool analysis of the patient.

FIG. 4 illustrates a urea concentration time profile of a typical patient as detected by the urea sensor 14. Applicants have discovered that the urea-concentration time profile can be closely matched to an early fit exponential curve 112 and to a late fit exponential curve 114. The two curves 112 and 114 are exponential fits of the urea concentration data pre and post thirty (30) minutes into the hemodialysis treatment. An empirically determined "inflection" point 116 is indicative of the differences in the fits 112 and 114, which is gradual shift caused by the two-pool nature of the urea removal from the patient's ICW 92 and ECW 94.

Initially in the hemodialysis treatment, the system 90 removes urea quite rapidly from the patient's blood and from the ECW 94 with which the blood 98 is in intimate contact. Thus, the initial fit 112, before the point 116 is a fairly steep slope. After a period of time, approximately thirty (30) minutes, enough urea is removed from the ECW 94 to create a urea gradient between the ICW 92 and the ECW 94.

At the point 116, the rate of urea removal from the ECW 94 decreases and the rate of urea removal from the cells in the ICW 92 increases. The latter is a result of a growing concentration differential between the ECW 94 and the ICW 92. The removal of urea from the patient's body is dependent upon the intercompartmental mass transfer area coefficient (iMTAC) (which controls mass transfer between the ICW 92 and ECW 94) and the dialyzer mass transfer area coefficient (dMTAC) (which controls the mass transfer between the ECW 94 and the dialysate flow). The iMTAC is typically smaller than the dMTAC which causes the concentration differential between the ECW 94 and ICW 92. Consequently, the fit 114 after the point 116 has a more flat slope, than the slope of the early fit 112. It is thus clear that a single-pool analysis is much less accurate than the two-pool behavior as determined by the present invention.

Figure 5:
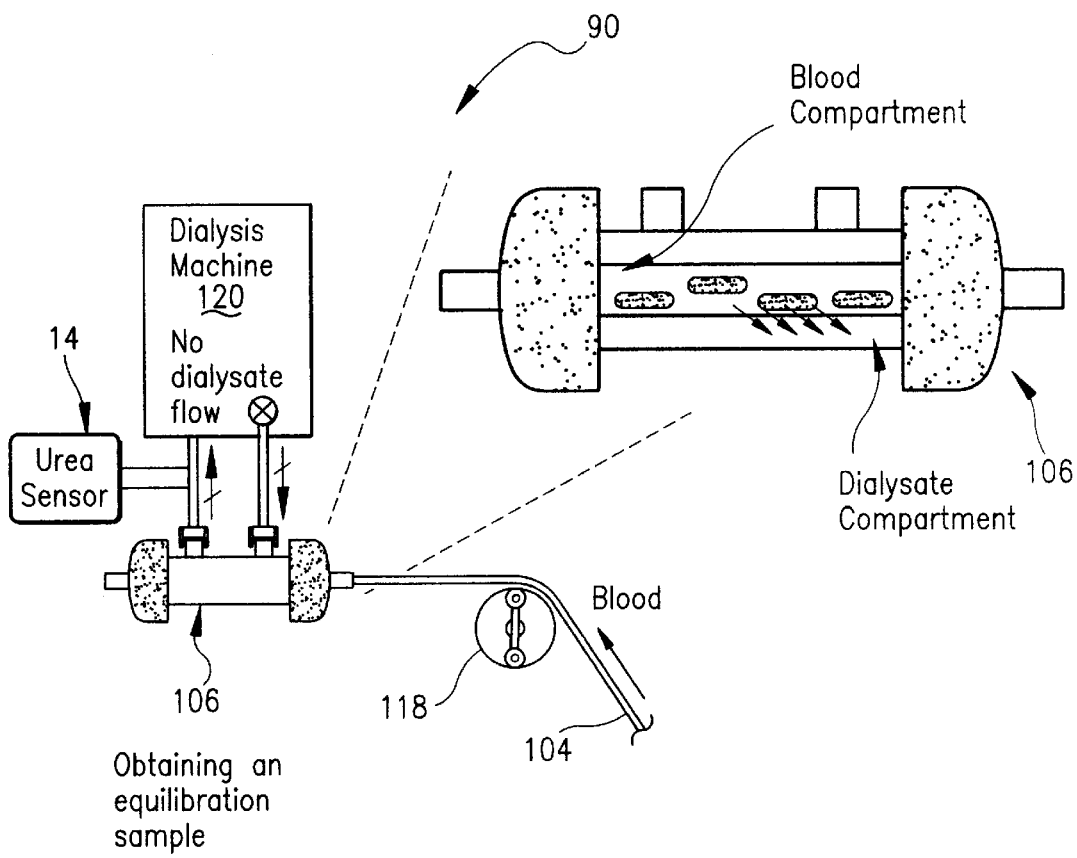
FIG. 5 is a functional block diagram illustrating the equilibration of the hemodialysis monitoring system.

The calculation of KT/V, URR, and SRI, employing the two-pool analysis in accordance with either of the systems 10 or 30, is as follows. In one preferred embodiment, prior to initiating the hemodialysis treatment, the hemodialysis monitoring system 10 or 30 of the present invention, for example purposes, is equilibrated with the patient's blood, as illustrated in FIG. 5. The blood is pumped to the dialyzer 106 via the line 104, such as by a roller pump 118. The dialyzer 106 is connected to and forms a portion of a conventional dialysis machine 120.

To obtain the equilibrated urea sample analysis, after initial filling of the dialyzer with dialysate, the dialysate flow is shunted past the dialyzer 106 or stopped, while the blood is pumped through the dialyzer 106. No dialysate flow is allowed between the dialyzer 106 and the dialysis machine 120, however, ultrafiltration does exist even with the dialysate flow in bypass. After an elapsed time period, such as five (5) minutes, during which the urea concentrations of the blood and the dialysate are allowed to equilibrate across the membrane, an equilibration sample is obtained and sensed by the urea sensor 14. The equilibration sample provides the urea concentration in the patient's blood before the dialysis treatment. The equilibrated concentration is utilized in conjunction with the dialyzer typical profiles, dialysate clearance (K), and total body water (V), to calculate KT/V, URR, nPCR, and the solute removal index (SRI).

Figure 6:
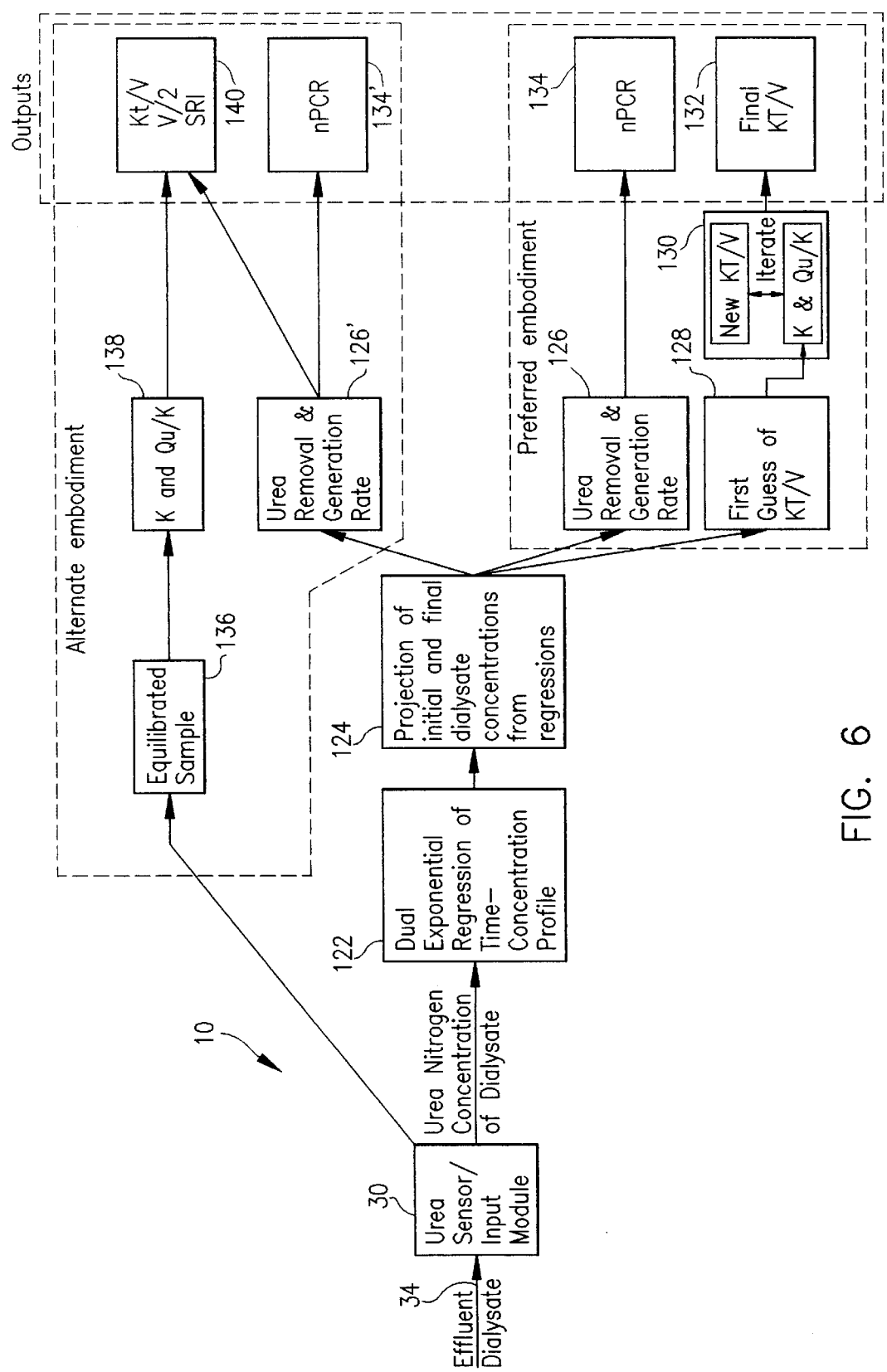
FIG. 6 is a flow chart of the preferred embodiments of the present invention.

Utilizing a first preferred embodiment of the hemodialysis monitoring system 10, without obtaining an equilibrated sample, the following steps are performed, as illustrated in FIG. 6:

1. Two exponential regressions of the concentration/time profile are performed, with the first regression fit covering the segment from zero to thirty (0–30) minutes, and the second regression fit covering the segment from thirty (30) minutes, to the current time as indicated by block 122.

2. The initial ($CD_1$) thirty (30) minutes ($CD_{30}$), current minute ($CD_t$), and final ($CD_2$) dialysate urea concentrations are projected from these regressions and the log mean dialysate concentration is calculated for each segment as indicated by block 124.

3. Urea removal for each segment then is calculated as the product of log mean dialysate concentrations, dialysate outflow (QDo) and segment time. These products are summed to obtain the projected urea removal (R) for the dialysis treatment as indicated by block 126.

4. Because of the typical unequal spacing of dialysis treatments over a seven (7) day period, urea removal for a given treatment is dependent upon the day of the week. A factor (F) was derived from a variable volume urea kinetic model utilizing a range of clearances (K), urea distribution volumes (V), urea generation rates (G), ulltrafiltration rates ($Q_u$), and treatment times (T). The projected weekly removal ($R_{wk}$) is calculated using F and R.

5. G (in mg/minute) then is calculated from $R_{wk}$.

6. $Q_u$ is calculated from total ultrafiltration and treatment time.

7. A "first guess" (estimate) for KT/V is calculated utilizing the formula $(KT/V)_{fg}$=LN $(CD_1/CD_2)$, with $CD_1$ and $CD_2$ projected from the exponential regressions of the time/concentration profile, as indicated by block 128.

8. K and $Q_u/K$ are calculated from $(KT/V)_{fg}$ and an estimate of V (as percentage of body weight; 51% for males, 43% for females).

9. $Q_uT/V$ and hence, a new KT/V, are calculated as indicated by block 130 utilizing the formula:

$$LN\left[1 + \frac{Qu*T}{V}\right] = \frac{Qu}{(K-Qu)} *LN\left[\frac{\left(CD_1 - \frac{G}{K-Qu}\right)}{\left(CD_2 - \frac{G}{K-Qu}\right)}\right]$$

10. A new K is calculated from the KT/V obtained in step 9.

11. Iteration of steps 9–10 is continued until convergence is obtained which results in a final KT/V as indicated by block 132.

12. The normalized protein catabolic rate (nPCR) then is calculated utilizing G and V, as indicated by block 134.

13. In lieu of KT/V, URR can also be reported as $1-CD_1/CD_2$.

Utilizing a second preferred embodiment of the hemodialysis monitoring system 10, after first obtaining an equilibrated sample, the following steps are performed, as also illustrated in FIG. 6. The dialysate sample has been equilibrated with blood before the dialysis treatment ($Cb_{equil}$) (as described elsewhere) as indicated by block 136:

1. Steps 1–6 are performed as above.

7. Clearance (K) is calculated directly from $Cb_{equil}$, QDo and $CD_1$, as indicated by block 138.

8. KT/V is calculated utilizing the formula in step 9 above, as indicated by block 140.

9. Kinetic volume of urea distribution ($V_2$) is calculated from KT/V (step 3), as indicated by a block 126' and K (step 2), as indicated by block 138.

10. Solute Reduction Index (SRI) represents the fraction of solute (urea) that has been removed from the total body stores by hemodialysis and is calculated as indicated by block 140 from:

$$SRI=[R-G*T(\text{dialysis})]/(V_1*Cb_{equil})$$

where $V_1=V_2+\text{ultrafiltration}$.

11. The normalized protein catabolic rate (nPCR) then is calculated utilizing G and V as before as indicated by block 134'.

12. In lieu of KT/V, URR can also be reported as $1-CD_1/CD_2$.

The first embodiment can be utilized when it is not possible or desirable to obtain an equilibration sample. The second embodiment can be utilized when it is possible to obtain an equilibration sample, especially when the system 10 is integrated with or is able to automatically control the hemodialysis machine.

As further embodiments:

1. The concentration/time profile also could be fit with a single exponential regression to project $CD_1/CD_2$, and R.

2. The concentration/time profile also could be fit with a non-linear regression (e.g., the sum of two exponentials). The exponents resulting from these regressions then would be utilized to calculate K, G, and V, utilizing standard two pool urea kinetics determined for blood urea concentration/time profiles.

3. Also, a percent urea reduction method utilized for blood urea concentrations (e.g., a formula of the type: KT/V= −LN [Cpost/Cpre-008*Time-Ultrafiltration/Weight]) could be utilized to calculate KT/V utilizing dialysate urea concentrations.

In the further embodiments, numbers 1 and 3 result in a KT/V that represents single pool urea kinetics, while the preferred embodiments, previously described and the further embodiment number 2, result in a KT/V that represents two pool urea kinetics.

The hemodialysis monitoring system 10 can draw a sample volume at any predetermined time period. It empirically has been determined that a time period on the order of every ten (10) minutes is sufficient for the hemodialysis treatment, since the urea concentration values change at a relatively slow rate. The rate change is sufficiently slow, such that continuous sampling is not required and intermittent sampling is sufficiently accurate to represent real time. Thus, sampling the dialysis effluent every five (5) to ten (10) minute periods provides a real time urea concentration profile. A convenient sample volume, utilizing the urea sensor 14 is on the order of two (2) milliliters (ml) of dialysate effluent. The hemodialysis monitoring system 10 can also provide an equilibrated urea concentration value at the end of the hemodialysis treatment.

Because of the technique of the hemodialysis monitoring system 10 of the present invention, after about sixty (60) to ninety (90) minutes of a three (3) to four (4) hour hemodialysis treatment, the final urea concentration value can be projected. This mid-treatment projection then can be utilized to troubleshoot the hemodialysis treatment, if the final projected KT/V result is too low.

In a typical patient, when the hemodialysis treatment is initialized, the patient's blood will contain on the order of seventy (70) milligrams (mg) of urea in one hundred (100) ml of blood. After four (4) hours of the hemodialysis treatment, the patient's blood will contain on the order of thirty (30) mg of urea in one hundred (100) ml of blood. On the dialysate side of the dialysate cartridge 106, the dialysate, after initiating treatment initially will contain on the order of twenty-five (25) mg of urea in one hundred (100) ml of dialysate. After the four (4) hours of the hemodialysis treatment, the dialysate will contain on the order of five (5) to seven (7) mg of urea in one hundred (100) ml of dialysate, since blood concentration decreases during the hemodialysis treatment.

The urea change is exponential, such that about one-half of the urea is removed in about one-third of the total hemodialysis treatment time period. Since the urea change is exponential, it is convenient to sample more frequently in the initial part of the hemodialysis treatment time period. For example, during a four (4) hour hemodialysis treatment, the hemodialysis monitoring system 10 can be set to sample every five (5) minutes in the first hour and then every ten (10) minutes during the rest of the hemodialysis treatment.

It has been empirically determined that the two-pool analysis of the hemodialysis monitoring system 10, as described with respect to FIG. 4, is on the order of twelve (12) to eighteen (18) percent more accurate then the conventional one-pool analysis. The hemodialysis monitoring system 10 also is set to monitor the dialysis effluent, only when the hemodialysis machine 120 is operating. Some prior art systems utilize a total clock period, without regard to dialysis shut down periods due to system alarms.

Further, as is described in more detail in the above cross-referenced application for a "FLUID SAMPLING MODULE," the hemodialysis monitoring system 10 is prevented from sampling the dialysate effluent during a period of no or very low dialysate effluent flow. Sampling during a period of no or unstable flow, also can introduce errors into the analysis treatment. Urea is a convenient marker to utilize in the hemodialysis treatment, since it is related to other uremic toxin levels, but other well-known markers also can be utilized in the hemodialysis treatment of the present invention as previously described.

The prior art hemodialysis monitoring treatment typically draws a blood sample from the patient (an invasive treatment), typically on the order of once a month. The urea concentration value then is utilized as the initial hemodialysis treatment value. The final or post hemodialysis treatment value is obtained from a blood sample taken after the end of the hemodialysis treatment. The urea concentration ratio from these two blood samples then is utilized to determine the efficiency of the hemodialysis treatment, which provides a KT/V value which is not as accurate as that obtained utilizing the present invention.

The prior art analysis is further inaccurate, because although the urea concentration in the ICW 92 attempts to equalize with that in the ECW 94, there is considerable time lag. The urea is removed rapidly from the blood, resulting in a significant differential between the urea concentration in the ICW 92 and in the ECW 94 at the end of the hemodialysis treatment. At the end of a typical hemodialysis treatment, urea concentrations can be about forty (40) mg/dl in the ICW 92, and about thirty (30) mg/dl in the ECW 94. Thus, since the ICW 92 has a total nominal volume greater than the ECW 94 total nominal volume, the final ECW 94 urea concentration value of about thirty (30) mg/dl can be very inaccurate. The single or one pool analysis does not take into account the difference between the final urea concentration in the ICW 92 and the ECW 94. Since the one pool analysis generally is based upon the urea concentration in the ECW 94, if an equalization or rebound period on the order of thirty (30) to sixty (60) minutes is not accounted for, the analysis will overestimate the true KT/V. Continued diffusion from the ICW 92 into the ECW 94 causes the concentration of the ECW 94 to rebound or increase with time.

The hemodialysis monitoring system 10 is described as a separate unit, which is attached to the lines of the dialyzer 106, which is part of the dialysis machine 120. The hemodialysis monitoring system 10 also can be retrofit to the dialysis machine 120, or can be fully integrated into the dialysis machine 120 without departing from the spirit or scope of the present invention.

Figure 7:
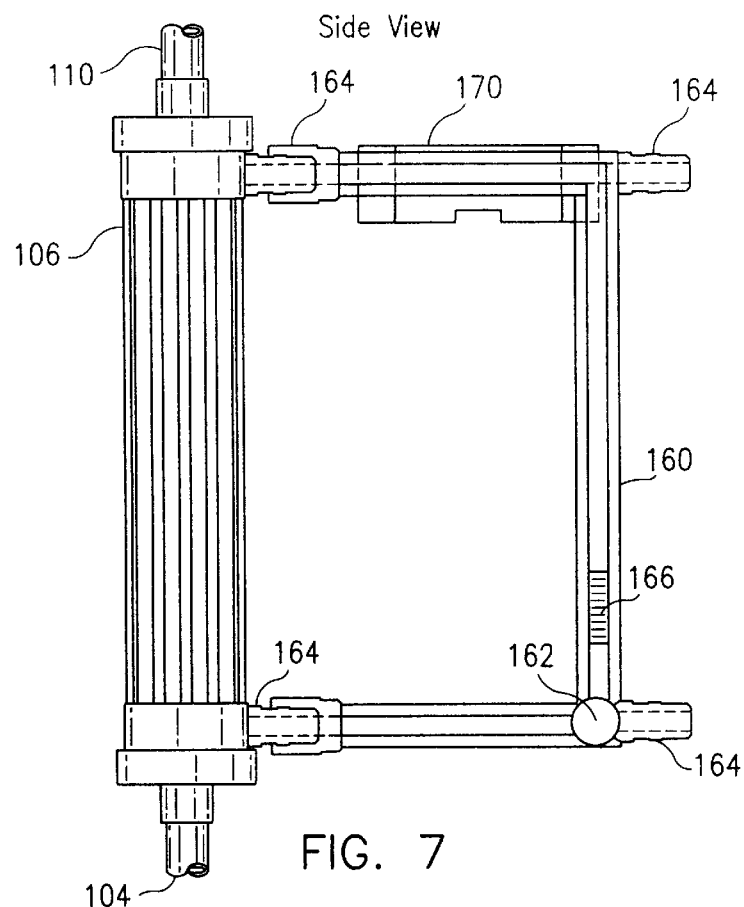
FIG. 7 is a side view of the device in accordance with the invention shown connected to a dialyzer.
Figure 8:
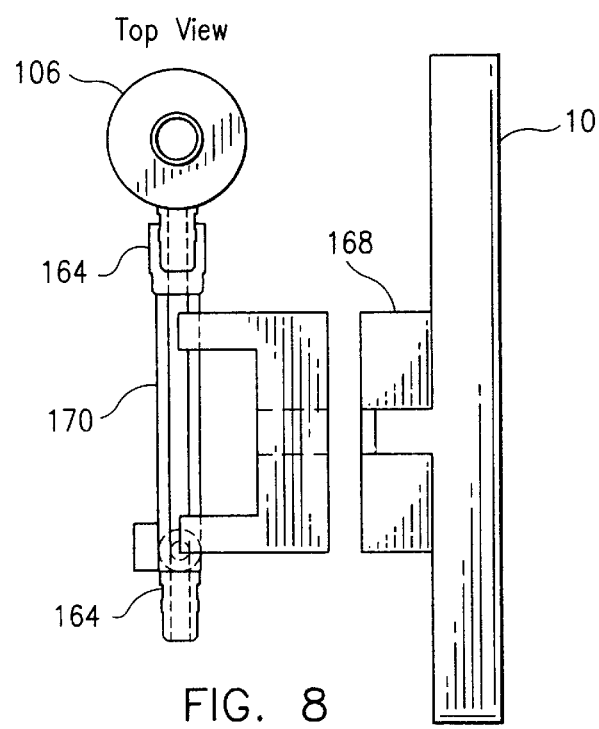
FIG. 8 is a top schematic view of the device of the invention shown connected to a dialyzer, and mounted on a dialysis machine.

In a further aspect of the invention with the apparatus shown in FIGS. 7 and 8, it becomes possible to obtain a plurality of pre-, post-, and mid-dialysis equilibrium samples on any dialysis machine. The device of FIGS. 7 and 8 can be, for example, attached to a dialysis machine such as that commercially marketed under the trade name Baxter Bio-Stat™ 1000, the sampling portion of which is described with reference to FIGS. 1–6, previously discussed herein. By obtaining such equilibration samples, and applying values from variables relating to the samples to certain equations as described hereafter, the intercompartmental transfer coefficient ($K_f$) for the two pool kinetics for a patient undergoing dialysis can be obtained to permit a much more precise adjustment of the prescriptive treatment for the patient undergoing dialysis.

The advantages obtained by the use of the device of FIGS. 7 and 8 become more readily apparent when viewed with reference to its use with the system of FIGS. 1–6. In a system such as described with respect to FIGS. 1–6, it is possible to obtain a pre-run equilibration sample by placing the dialysis machine in bypass mode, and waiting a fixed period of time, for example, five (5) minutes, to obtain an equilibration sample which is used to obtain separate estimates of whole body clearance, i.e., K, and the volume of urea distribution, i.e., V. However, in doing this with the system of FIGS. 1–6, a number of difficulties are encountered. More specifically, manual intervention by the nurse or patient-care technician is required to place a dialysis machine in a bypass mode. Further, manual intervention is also required to take the dialysis machine out of bypass, which in a busy dialysis unit may not always be possible in spite of various alarm conditions being indicated. It is also assumed that the dialysis machine has a small enough dialysate loop that equilibration of the blood within the dialysate can occur in a reasonable amount of time.

While generally this is possible if the equilibration volume is on the order of the size of the dialyzer dialysate compartment with a small amount of added tubing, i.e., approximately 150 milliliters, in the case of machines such as the German DT or the Hospal machine, larger or very large dialysate loops on the order of greater than 150 milliliters are encountered so that equilibration takes much longer than five (5) minutes, an amount of time which may be unacceptable in an ongoing dialysis treatment. Further, post-run equilibration samples require additional manual intervention, and as a result may be either intentionally or inadvertently omitted even though they provide additional useful information for purposes of modifying and/or validating the prescribed treatment.

With respect to the methodology employed in the use of the system described with respect to FIGS. 1–6, it is assumed the dialysate and blood concentration time profiles are parallel. This implies that clearance remains constant throughout a dialysis run. There is a potential, although highly infrequent possibility that clearance may change slowly over the course of a run as result of dialyzer clotting. This would in turn cause KT/V to be overestimated.

In accordance with the device of the invention, mid-run clearance checks can be performed, thereby minimizing the possibility that KT/V is overestimated. Another problem encountered with the system of FIGS. 1–6 is that it requires that the technician know the dialysate flow rate and calculate the known flow rate and manually input it for the KT/V calculations. The user must then collect outflow dialysate for a period of time and/or rely upon the flow calibration of the machine. Machines have been found, however, to have different flow rates throughout a dialysis run. Further, it is also possible that dialysate outflow collection is inconvenient at the time required so that erroneous data is often used.

In order to avoid these problems, in accordance with the invention, there is provided a bypass loop apparatus 160 as shown in side view in FIG. 7 and top view in FIG. 8. Other than the addition of the bypass loop apparatus 160 which connects between the dialyzer 106 and the delivery system, the system is the same as that shown and described with reference to FIGS. 1–6.

Figure 9A:
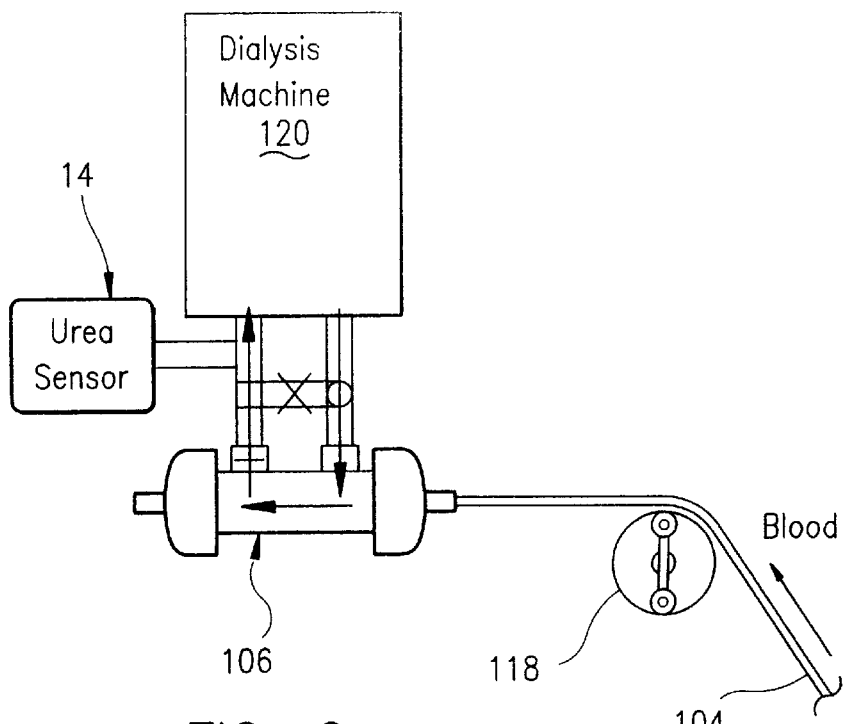
FIG. 9A and 9B are views similar to FIG. 5 showing the device of the invention on a hemodialysis monitoring system, and respectively shown in a normal flow condition, and during equilibration.
Figure 9B:
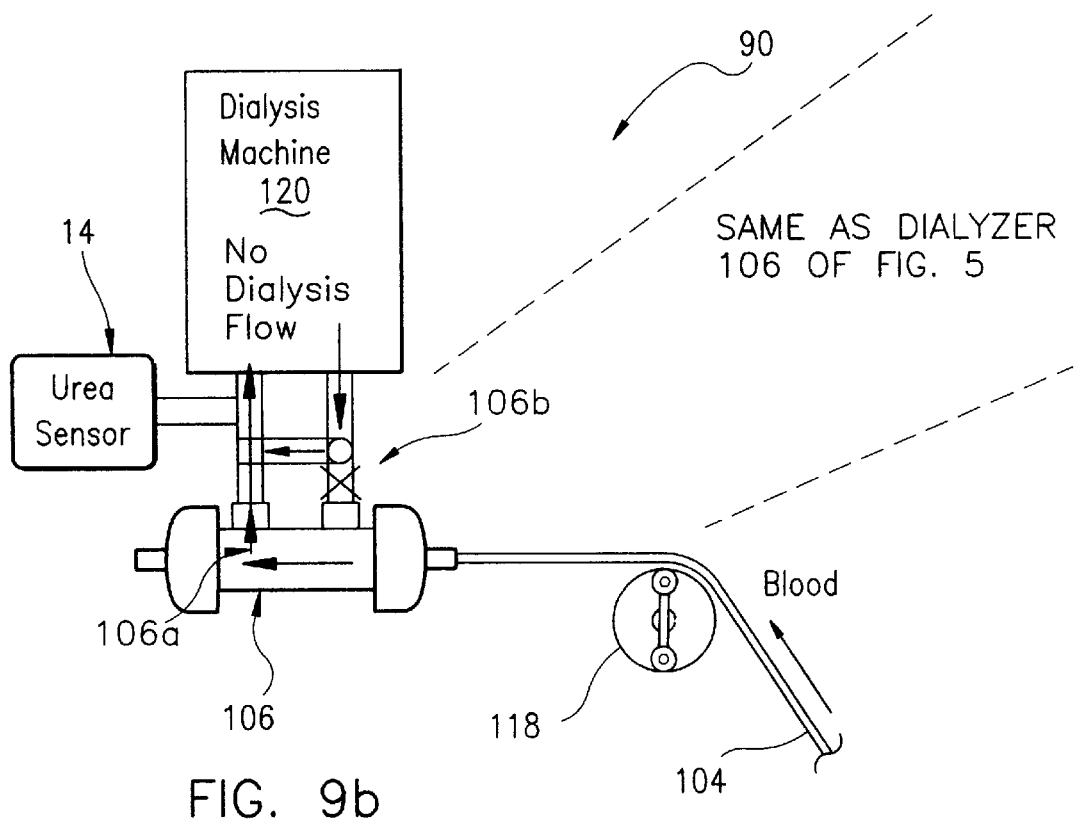

More specifically, the modification illustrated can be done, for example, on a urea monitor, such as the Baxter BioStat 1000™ urea monitor, to include a semiautomatic bypass system to allow automation of the equilibration sample. More specifically, the device is made up of a valve and flow detector which is connected, for example, to a Baxter BioStat 1000™ urea monitor as illustrated in FIGS. 9A and 9B. As will be appreciated, although the device of the invention is described with specific reference to the Baxter BioStat 1000™ urea monitor, it will be readily apparent to those of ordinary skill in the art that it can also be used with other urea monitors to automate the operation thereof. In use, when an operator energizes the device from its keypad, a valve opens and bypasses the dialyzer by directing dialysate flow back to the machine as is more clearly seen with reference to FIGS. 9A and 9B, described in greater detail hereafter in the text.

With respect to FIGS. 7 and 8, the bypass loop apparatus 160 is connected to a dialyzer cartridge or dialyzer 106 through standard couplings 164 such as Hanson connectors. A solenoid valve serves as a bypass valve 162 to divert dialysate flow through a flow meter 166, so as to allow the dialysate in the dialyzer 106 to equilibrate with the blood plasma water which is pumped through the blood side of the dialyzer 106. Dialysate in the dialyzer 106 remains at the set membrane pressure through the connecting arm 170 which allows the aforementioned ultrafiltrate to be sampled by the hemodialysis monitoring system 10. As further shown in FIG. 8, the bypass loop apparatus 106 can be mounted on a saddle member 168, which is mounted on the dialysis monitoring system 10, which allows the entire unit to be assembled in a compact manner. Flow meter 166 allows reading of volumes of dialysate being passed through the dialysis machine to enable calculation of the various values necessary to the proper operation of the system and method in accordance with the invention.

In accordance with the method of the invention, the bypass loop apparatus 160 which is attached to the dialysis machine and dialyzer 106 permits bypassing of the dialyzer 106 under conventional software control and appropriate conventional mechanical/electrical connections to permit blood to equilibrate with a smaller than normal dialysate pool in the dialyzer 106. This permits a dialysate sample to be taken which has the same plasma water concentration of a metabolite as the blood, i.e., what is conventionally known as an "equilibrium" or "equilibration" sample.

In accordance with the invention, the equilibration sample can be used in various ways. Initially, it is desired to use a pre-run equilibration sample to separate the values for K and V as previously described herein with reference to FIGS. 1–6. In addition, the rate at which the blood urea nitrogen (BUN) concentration rises in the blood, from corresponding post-run equilibration samples after dialysis treatment, is directly related to the intracellular to extracellular transfer rate of metabolite within the body of the patient. This rate has previously been described herein as the two-pool intercompartmental transfer coefficient which is used to predict the effect of intervention or changes in a dialysis treatment to improve dialysis efficiency. Further, a mid-run equilibration sample can be used to check dialyzer clearance to ensure that slow changes in clearance due to, for example, clotting, are not occurring.

In accordance with the system and method described previously with respect to FIGS. 1–6, it is important that the user of the hemodialysis monitoring system know the dialysate flow rate (e.g., 200 ml/minutes) in order to determine the adequacy of dialysis. This requires that the user collect out flow dialysate for a given period of time and/or rely upon the initial flow calibration of the machine. However, as previously noted, since these types of machines frequently have different flow rates and/or collecting dialysis out flow is inconvenient, erroneous data is often obtained. Thus, in accordance with the use of the flow meter 166, it become possible to immediately determine what the dialysis flow rate is at any time that equilibration is being conducted.

In accordance with the device of FIGS. 7 and 8, the dialysis flow bypass can be created by placing solenoid value 162 in the bypass position. This bypassed dialysate flows away from the dialyzer 106 allowing the dialysate compartment of the dialyzer 106 to equilibrate with blood passing therethrough. No manual intervention is required therefore to run equilibration samples, before, during, or after a dialysis run. The multiple equilibration samples obtained can be used to calculate the intercompartmental transfer coefficient of a particular patient, i.e., ($K_I$), as well as do a separate mid-run check of the dialyzer 106 clearance (K). In addition, the dialysate flow can be read directly from the apparatus 160 by viewing the flow meter 166, as opposed to relying upon timed collections or manual entry. The apparatus of FIGS. 1–6 can be used in conjunction with the apparatus of FIGS. 7 and 8 to measure the metabolite in the equilibrated dialysate.

In accordance with the method of the invention employing the device of FIGS. 7 and 8, it becomes desirable to obtain the intercompartmental transfer coefficient $K_I$ of a patient, because while not strictly necessary to perform dialysis or to assess dialysis adequacy, it provides valuable information as to how a given intervention will affect outcome. For example, a higher KT/V can be obtained by either increasing K or T. Increasing time, which as previously noted, involves increased staff time and poor utilization of dialysis facilities, is usually done as a secondary option to increasing clearance (K). Clearance can be raised, for example, by increasing blood flow or dialyzer 106 size.

In the case of patients having an extremely low intercompartmental transfer coefficient ($K_I$), they will not respond adequately to just an increase in clearance. Knowing $K_I$, however, will permit a user/technician to more accurately ascertain the effects of a given intervention on the dialysis prescription.

Under the system described with reference to the device of FIGS. 1–6, a physician or dialysis nurse/technician must measure KT/V, change the prescription, measure KT/V again, and make another prescription change, and so on, until an optimum therapy for the patient is obtained. By knowing the two-pool parameters explicitly, i.e., the intercompartmental transfer coefficient $K_I$ of a patient, this allows the number of interactions necessary to obtain an optimum prescription to be decreased. A consequent advantage is that a more efficient use of staff time and lab facilities is obtained.

In operation, when it is desired to equilibrate dialysate in the dialyzer 106, the bypass solenoid valve 162 is actuated. This shuts the flow off from the bottom of the dialyzer 106 and reroutes it through the flowmeter 166 in the central column where it is subsequently returned to the dialysis machine. The flow through the central column of the flowmeter 166 maintains the system at a transmembrane pressure set by the dialysis machine. This causes the ultrafiltration which facilitates the equilibration of the dialysate with the blood flowing through the dialyzer 106. In a further construction, the bypass apparatus 160 can be constructed in a telescoping arrangement to account for different size dialysis cartridges 106.

Figure 10:
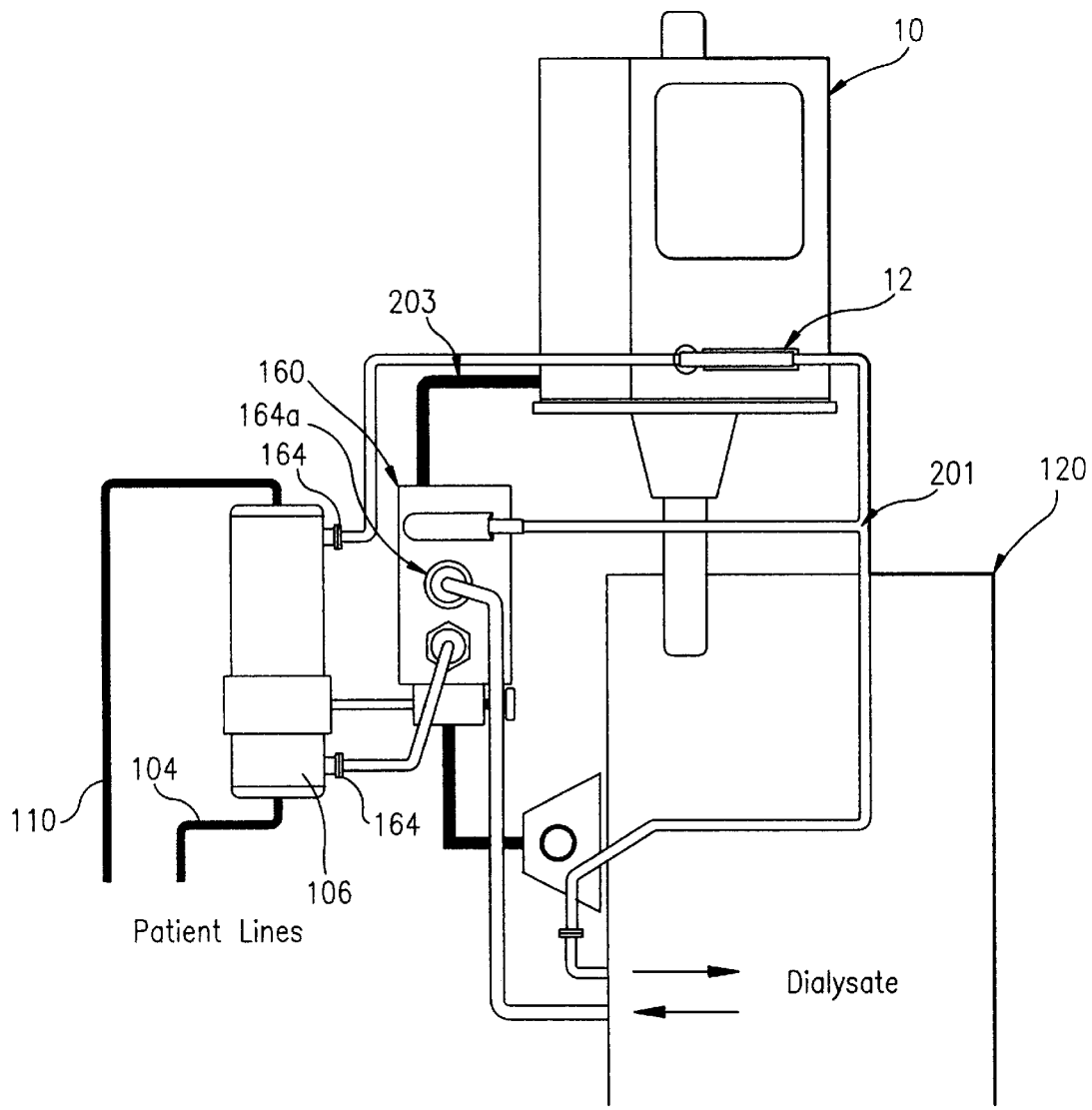
FIG. 10 is a detailed diagram showing alternate actual connections between the device of the invention, and a urea monitor, such as the one commercially available from Baxter Healthcare under the name BioStat 1000™ M, and a dialyzer.
Figure 11:
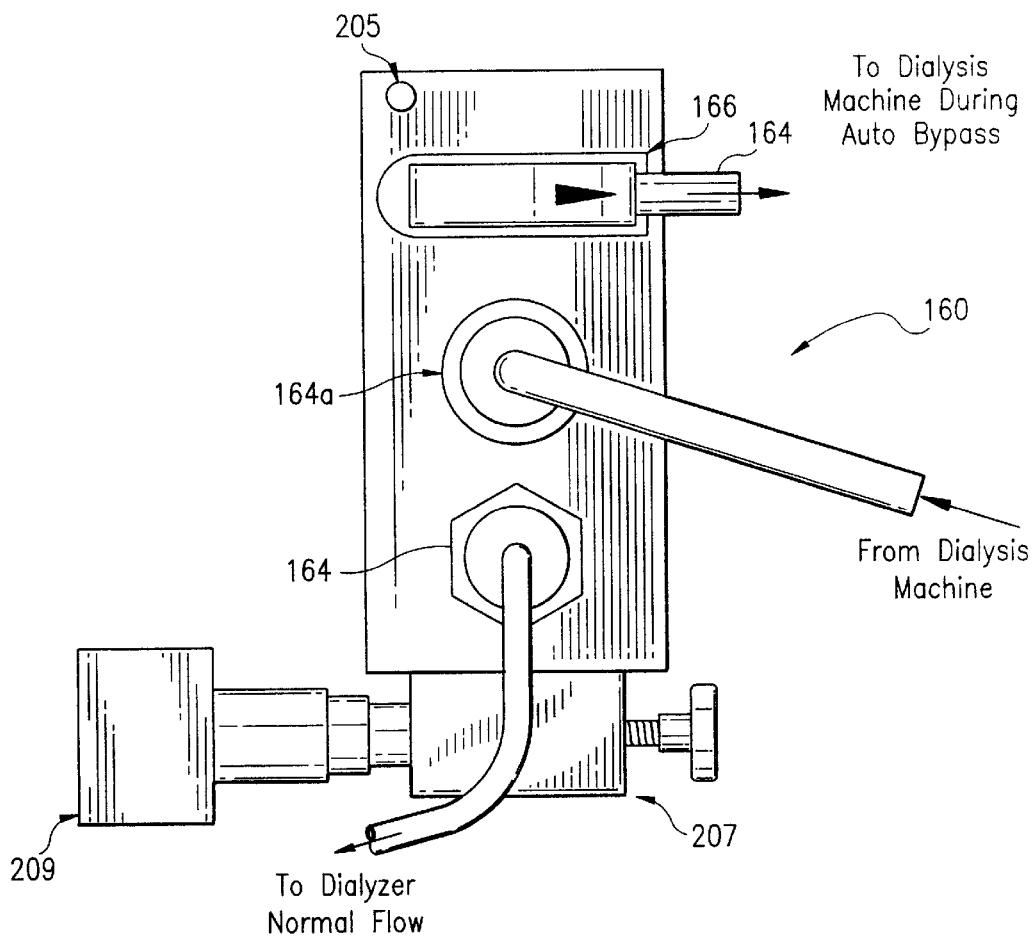
FIG. 11 is an enlarged view of the device of FIG. 10.

FIGS. 10 and 11 illustrates an alternative embodiment of the device of the invention. In this embodiment, a bypass valve/unit 160 is connected to the dialysate inflow line, at a Hansen-type connection 164a. From there, depending upon the position of bypass valve apparatus 160, dialysate flows to dialyzer 106 to which the bypass valve apparatus is connected at connector 164, or bypasses the dialyzer 106 to be caused to flow through a flow meter 166 connected at connection 164 to the dialysis machine during automatic bypass. A status light 205 indicates apparatus 160 position. The bypass valve apparatus 160 is mounted to the dialysis machine 120, for example, through a mounting block 207 onto a rod thereof, and the dialyzer clamp 209 serves to hold the dialyzer 106. In bypass mode, flow from the bypass valve apparatus 160 connects at a T connection 201 to return dialysis flow to the dialysis machine 120 at a mounting pole.

As seen from the description of the two embodiments of the device of the invention, the bypass system is made up of two major components. A first component is the bypass apparatus 160, and a second part is the bypass tube set, for example, as the tubes shown with replaceable tubes connected to the various units through Hansen connectors 164 and 164a. The bypass apparatus 160 includes a valve, the flow detector 166 (replaceable), and a saddle therefor, and the status light 205.

In accordance with the method of the invention, an equilibration sample can be obtained by placing the dialysis machine into bypass mode by activating valve 162 to produce a dialysate bypass with the blood pump running. Ultrafiltration and diffusion take place from the blood compartment of the dialyzer 106 to the dialysate compartment so that after a set equilibration time ($t_{equil}$), the dialysate concentration in the dialyzer 106 would be the same as the plasma water concentration of the blood. Since $t_{equil}$ is not necessarily known, however, dialysate samples are taken sequentially until the measured concentrations only differ by a small amount ($C_{Delta}$). The higher of the last two samples is then assumed to be the equilibration sample. This procedure can be followed prior to, during, or after the completion of dialysis. When performed during or after dialysis $C_{Delta}$ is less than $C_{Delta}$ prior to the start of dialysis due to the fall in BUN.

Preferably, one equilibration sample will be taken at the beginning of dialysis in order to separate clearance (K) from the volume of urea distribution (V). One may also be taken midway through the dialysis session to assure the performance of the dialyzer by obtaining another measurement of K to compare with the initial measurement. Three or more additional equilibration samples ($C_t$) taken serially at specified intervals after the completion of dialysis, or after the blood pump is shut off midway through dialysis, will allow the intercompartmental transfer coefficient ($K_I$) to be obtained. Generally the sampling interval would be every five (5) minutes, although shorter time intervals (e.g., two (2) minutes) could be used to reduce the total time the patient is in the unit. Thereafter, the following equation is fit, using non-linear fitting techniques in a conventional manner with the multiplicity of post-dialysis equilibration samples:

$$C_t = C_0 + (C_\infty - C_0)e^{(-\gamma t)}$$

In the above equation, $C_t$ is the post-dialysis equilibration concentration at time t, where zero time is the end time of dialysis, $C_0$ is the concentration immediately post-dialysis (which is an immeasurable value since a given concentration value requires a finite equilibration time and there will have been no equilibration time immediately post dialysis), $C_\infty$ is the concentration at infinite time and $\gamma$ is a time constant. With at least three (3) equilibration samples, $\gamma$, $C_0$, and $C_\infty$ can be obtained from the fitting procedure. The urea generation rate and residual renal function are not included in this formula. Alternative forms of this fitting equation are:

$$C_t = C_t + (C_\infty - C_0)e^{(-\gamma t)}$$

$$C_t = C_0 + (C_\infty)e^{(-\gamma t)}$$

These can also be used to obtain $\gamma$, depending upon the number of equilibration samples available.

The intercompartmental transfer coefficient can be then obtained from the following function: ($K_I = \gamma V_e V_i / V_T$).

Where $V_e$ and $V_i$ are the intra- and extra-cellular volumes respectively, and $V_T$ is obtained using the pre-dialysis equilibration sample and the algorithm previously described with reference to FIGS. 1–6. The variables $V_e$ and $V_i$ are assumed to have the ratio $V_e/V_i = R_v$ where $R_v$ is typically 2/3.

Alternatively, by using the device of FIGS. 7 and 8, $K_I$ can also be obtained by obtaining equilibration samples as before, by initially placing the dialysis machine into bypass with the blood pump running so that ultrafiltration and diffusion can take place to equilibrate dialysate in the dialyzer 106 and then sampling until successive measured concentrations differ by only a small amount. At least one, but preferably two or more equilibration samples ($C_t$), can then be taken during but preferably after the end of dialysis. Thereafter, this method differs in that unlike the previously described situation which determined $K_I$ based purely on data obtained during a period when dialysis has ceased, e.g., when the blood pump is shut off, the intra-dialytic concentration information is also used to calculate $K_I$. This will tend to give more reliable estimates of $K_I$ and is to be preferred over the earlier method. Moreover, unlike the previously described situation where the ratio of $V_e$ to $V_i$ is assumed to have a specific value, nonlinear-fitting techniques can also be used to compare the dialysis and post-dialysis concentrations of metabolite to the measured concentrations to obtain the best value for $K_I$ and $V_e/V_i$, assuming current values for G, K, $K_R$, and $V_T$. These values are obtained using the pre-dialysis equilibration sample and the algorithm previously described with reference to FIGS. 1–6.

More particularly, the equations set forth below are solved for the concentrations $C_e$ and $C_i$, where $C_e$ is the concentration in the extracellular compartment and $C_i$ is the concentration in the intracellular compartment, so that for given values of $K_I$ and $V_e/V_i$, SSQ is minimized. SSQ is the sum of the square of the differences between $C_e$ and the equivalent measured blood concentrations ($C_{Beq}$) during dialysis and the equilibration concentrations ($C_{eq}$) after dialysis. $C_{Beq}$ is obtained from the measured dialysate concentrations.

By solving the following equations during dialysis:

$$\frac{d(V_e C_e)}{dt} = G - K_I(C_e - C_i) - K(C_e - C_D) - K_R C_e$$

$$\frac{d(V_i C_i)}{dt} = +K_I(C_e - C_i)$$

and, after dialysis, the equations;

$$\frac{d(V_e C_e)}{dt} = G - K_I(C_e - C_i) - K_R C_e$$

$$\frac{d(V_i C_i)}{dt} = +K_I(C_e - C_i),$$

where at $t=0$, $C_e = C_i = C_{eo}$, SSQ can be minimized in accordance with:

$$SSQ = \sum_{i=1}^{i=n}(C_{Beq} - C_e)^2 + \sum_{j=1}^{j=m}(C_{eq} - C_e)^2,$$

where $C_{Beq} = (C_D \text{measured} * Q_{Do})/K$, and $Q_{do}$ is the dialysate flow rate including ultrafiltration, and $C_{eq}$ is the post dialysis equilibration concentration.

SSQ may be minimized through a variety of numerical techniques and the best fitting values of $K_I$ and $R_V$ are each varied through their appropriate ranges (200–1,600 ml/minutes for $K_I$) and (0.5 to 0.9 for $R_V$) in specific increments, and SSQ is computed for each pair of values. The best value for $K_I$ and $R_V$ is then the pair of values which result in the minimum SSQ. The limitation of this technique is that many calculations are required if the increment is small. For example, if $K_I$ is varied in 50 ml/minute increments and $R_V$ is varied in 0.05 increments, then 28×8 or 224, computations of SSQ have to be performed. Further, if it is desired to obtain estimates of $K_I$ and $R_V$ that are more precise than the given increments, then a more elaborate method needs to be employed, as will be readily apparent and known to those of ordinary skill in the art. Such methods can include conjugate gradient methods, quasi-Newton methods, downhill simplex methods, and direction-set methods. All such methods allow the parameters to be predicted, i.e., $K_I$ and $R_V$, to be varied in a predictable fashion so that precise values may be determined.

In summary, the invention describes an apparatus which allows an equilibration sample to be automatically obtained on any type of hemodialysis machine thereby eliminating operator error and verifying the constancy of "K" (and thus the lack of gradual dialyzer clotting). This, in turn, allows two useful kinetic parameters to be obtained by the methods outlined above, i.e., $K_I$, or the intercompartmental transfer coefficient, and $R_V$, or the ratio of the extra- to intra-cellular volumes. Moreover, since the total volume is known, knowing $R_V$ also implies explicit knowledge of the actual intra- and extra-cellular volumes.

Knowing $K_I$ is not strictly necessary to perform dialysis or assess dialysis adequacy, however, it provides valuable information as to how a given intervention will affect outcome. For example, a higher KT/V can be obtained by either increasing K or T. Increasing time (which implies increased staff time and poorer utilization of dialysis facilities), however, is usually done secondary to increasing clearance (K) which can be raised, for example, by increasing blood flow, dialysate flow or dialyzer size. Patients with an extremely low intercompartmental transfer coefficient ($K_I$) will not, however, respond adequately to purely an increase in clearance. Knowing $K_I$, however, will enable a user to ascertain a priori the effect of a given intervention on the dialysis prescription, measure the KT/V again, make another prescription change, etc., in order to obtain an optimum therapy for the patient. Knowing the two-pool parameters (i.e., intercompartmental transfer coefficient) for a given patient will decrease the number of iterations necessary to obtain an optimum dialysis prescription. This will make more efficient use of staff time and laboratory facilities.

Knowledge of $R_V$ gives some indication of the state of patient hydration. Generally, dialysis patients have expanded extracellular volumes which consequently results in a higher value of $R_V$. If, however, $R_V$ is low, the probability of intra dialytic hypotension increases. Knowing $R_V$ can help to avoid this. Even more important is the value of the intra-cellular volume which can be obtained from $R_V$. The latter parameter is an indication of body cell mass. When dialysis patients are maintained on hemodialysis for an extended period of time, there is often "wasting" or a shrinkage of the muscle mass. By tracking intra-cellular volume over time, nutritional interventions can be made before malnutrition becomes a significant problem.

With respect to use of the device of the invention at the start of treatment, the following steps and display sequence are followed for screen 1.

|  |  |
|---|---|
| Screen 1: | Equil. Sample?<br>Yes  No  Home |

Selecting "Yes" automatically turns on the bypass apparatus 160 valve. The following screens appear to prompt the user to correctly adjust the blood pump and dialysis machine. Each screen is a two-line display.

|  |  |
|---|---|
| Screen 2: | Establish Blood Flow<br>Done  Home |
| Screen 3: | Establish UF<br>Done  Home |
| Screen 4: | Equilibrating XX:XX<br>Cancel |

In the equilibration sequence, a clock in the system counts up and the urea monitor takes its first sample at two (2) minutes and continues to sample every two (2) minutes until the change in concentration between two (2) consecutive samples is two (2) mg/dl or less when the procedure is performed prior to the start of dialysis, or less than a proportionately smaller difference when the procedure is performed later in the dialysis treatment when the level of BUN has fallen. The urea monitor uses the higher of the last two samples as its equilibration sample result, prints the equilibration result and automatically turns off the bypass apparatus 160 valve and starts the treatment clock. If the concentration difference between two (2) samples does not fall below the specified minimum concentration difference by the end of the twelve (12) minute sample (12 minutes is the maximum time for equilibration with the bypass apparatus 160 valve), the urea monitor then prints "Equil. unsuccessful," and automatically turns off the bypass apparatus 160 valve, and starts the treatment clock. Sensors and safety devices of a conventional nature are incorporated to alert a user of a bypass apparatus 160 valve failure.

EXAMPLE

Experimental Procedure

In one example, twenty (20) hemodialysis patients were enrolled in a feasibility study. Patients were studied during the first fifteen (15) minutes of a single dialysis session. A two (2) ml blood sample was taken from the patients' access device after needles were in place. The patients were then put on dialysis in a normal manner. Prior to the start of the run, a bypass apparatus 160 valve was connected to the inflow and outflow dialysate lines of the dialysis machine 120. The apparatus 160 valve bypassed dialysate from the dialyzer 120 from reaching the cartridge 106. Upon initiation of dialysis, the urea monitor commenced sampling the equilibrated dialysate. As soon as the measured urea concentration became constant, the concentration was recorded, and the bypass apparatus 160 valve shut off or removed to allow the dialysis session to continue as normal.

Test Results

Figure 13:
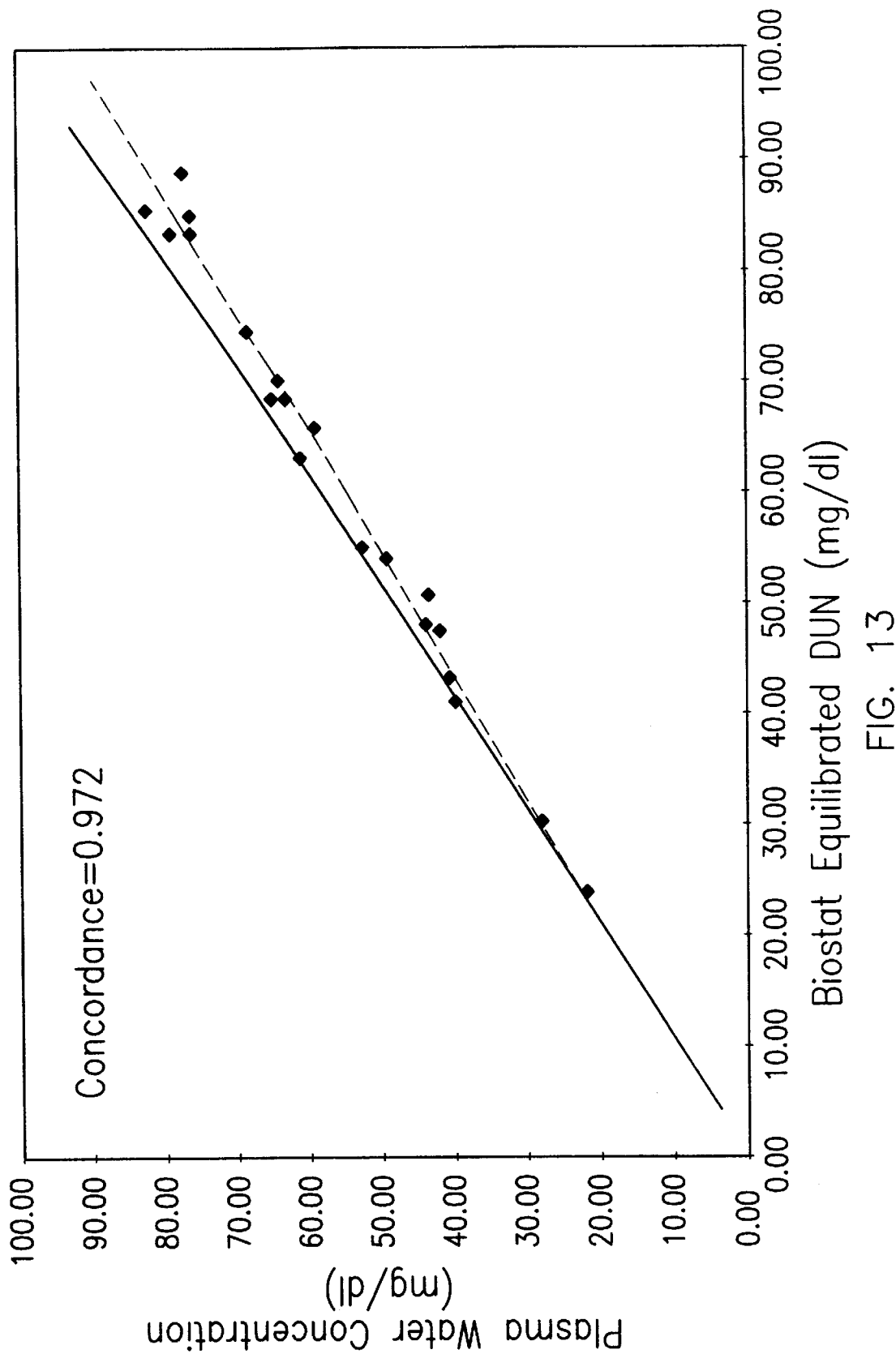
FIG. 13 is a graph showing the relationship between plasma water concentration and equilibrated DUN using the device of the invention.

The average time it took for the urea sensor to obtain an equilibration result was about 4.8 minutes, with a range of four (4) to eight (8) minutes (the manual method sets seven (7) minutes as a standard), and an average ultrafiltration rate of 17.5 ml/min., with a range of 2.8 ml/min. to 28 ml/min. FIG. 12 shows in table form the predialysis urea concentration as measured by the modified urea sensor of the invention, with the bypass valve system, compared to BUN measured in a clinical laboratory by use of the commercially available analyzer known under the trade name "Beckman CX3 analyzer," and the plasma water corrected labortory results (measured BUN divided by 0.93). The equilibration results and the plasma water corrected results are highly correlated (r=0.993) and concordant (CCC=0.972), with an accuracy factor of 0.978, as shown in the graph of FIG. 13. No mechanical problems or unsuccessful equilibration procedures were encountered.

Conclusion

Without the device of the invention, prior art urea sensors/monitors have encountered problems with the equilibration sample. The use of the device of the invention has avoided these problems and freed the user to tend to other clinical duties, thereby reducing the possibility of errors.

Having generally described the invention, the same will become better understood from the attached claims in which the invention is described in a non-limiting manner.

What is claimed is:

1. An apparatus for conducting equilibration of dialysate with a patient's blood for a patient undergoing hemodialysis, comprising
    connecting means for connecting to a dialysis machine for receiving a flow of dialysate therefrom and for connecting said flow to a dialyzer cartridge and directing a flow of dialysate from said dialysis machine through said dialyzer cartridge and back to said dialysis machine;

valve means actuatable between one position for stopping dialysate flow from said dialysis machine to said dialyzer cartridge and for directing said dialysate flow back to said dialysis machine, and for retaining a predetermined volume of dialysate in said dialyzer cartridge, and another position for allowing ultrafiltration to take place from the blood of the patient flowing through said dialyzer cartridge, with said returned pre-determined volume of dialysate remaining in said dialyzer cartridge ;

means for measuring the metabolite concentration in at least two samples of said retained pre-determined volume of dialysate and for continuing to sample said retained predetermined volume of dialysate until the difference in concentrations between two successive samples is less than a specified amount.

2. The apparatus in claim 1 wherein said means for measuring comprises a urea sensor.

3. The apparatus as in claim 1 further comprising flow measuring means for measuring the flow of dialysate from said dialysis machine when said valve means is in the another position for retaining said pre-determined volume.

4. The apparatus as in claim 1 wherein said valve means comprises a solenoid valve.

5. The apparatus as in claim 1 further comprising a flow meter for measuring the flow of dialysate diverted away from said dialyzer cartridge and to said dialysis machine by said valve means.

6. An apparatus for conducting equilibration of dialysate with a patient's blood for a patient undergoing hemodialysis, comprising:

first dialysis connecting means for connecting to a dialysis machine for receiving a flow of dialysate therefrom;

first dialyzer connecting means for connecting said first dialysis connecting means to one end of a dialyzer cartridge and for directing said flow of dialysate from said dialysis machine to said dialyzer cartridge;

second dialyzer connecting means for connecting to another end of said dialyzer cartridge for directing said flow of dialysate from said dialyzer cartridge;

second dialysis connecting means for connecting said second dialyzer connecting means to said dialysis machine for directing said flow of dialysate from said dialyzer cartridge through said second dialyzer connecting means into said dialysis machine;

bypass means selectively actuatable between two positions, a first position in which the flow of dialysate is directed from said dialysis machine, through said first dialysis connecting means, through said first dialyzer connecting means, through said dialyzer cartridge, through said second dialyzer connecting means, and through said second dialysis connecting means for being returned to said dialysis machine, and a second position in which the flow of dialysate is shunted after passing through said first dialysis connecting means. before passing to said first dialyzer connecting means, for directing dialysate flow away from said dialyzer cartridge to said second dialysis connecting means for being returned directly to said dialysis machine without passing through said dialyzer cartridge; and means for selectively sampling dialysate from said dialyzer cartridge when said bypass means is in said second position for measuring the concentration of metabolite in a selected sample of dialysate from the dialyzer cartridge.

7. The apparatus as in claim 6 further comprising flow measuring means for measuring the flow of dialysate from said dialysis machine when said bypass means is in said second position.

8. The apparatus as in claim 7 wherein said flow measuring means comprises a flow meter.

9. The apparatus as in claim 6 further comprising mounting means for mounting the apparatus on a dialysis machine.

10. The apparatus as in claim 6 wherein said bypass means comprises a solenoid valve.

11. The apparatus as in claim 6 wherein said means for selectively sampling comprises a urea sensor.

* * * * *